(12) United States Patent
Djokovic et al.

(10) Patent No.: US 11,294,464 B2
(45) Date of Patent: Apr. 5, 2022

(54) ADAPTING MEDIA CONTENT TO A SENSED STATE OF A USER

(71) Applicant: TRIPP, Inc., Venice, CA (US)

(72) Inventors: Andreja Djokovic, Chicago, IL (US); Zachary Norman, Venice, CA (US); Nanea Reeves, Marina Del Rey, CA (US); Joseph P. Uildriks, Tinley Park, IL (US); Walter John Greenleaf, Portola Valley, CA (US)

(73) Assignee: TRIPP, Inc., Venice, CA (US)

( * ) Notice: Subject to any disclaimer, the term of this patent is extended or adjusted under 35 U.S.C. 154(b) by 0 days.

(21) Appl. No.: 16/283,304

(22) Filed: Feb. 22, 2019

(65) Prior Publication Data

US 2019/0258315 A1 Aug. 22, 2019

Related U.S. Application Data

(60) Provisional application No. 62/634,120, filed on Feb. 22, 2018.

(51) Int. Cl.
*G06F 3/01* (2006.01)
*A61B 5/024* (2006.01)
(Continued)

(52) U.S. Cl.
CPC .......... *G06F 3/015* (2013.01); *A61B 5/02444* (2013.01); *A61B 5/721* (2013.01); *G06F 3/011* (2013.01); *G06F 3/0346* (2013.01); *G06F 3/14* (2013.01); *G06F 3/167* (2013.01); *G06F 13/161* (2013.01); *G09G 3/20* (2013.01);
(Continued)

(58) Field of Classification Search
CPC ........ G06F 3/015; G06F 3/165; G06F 13/161; G06F 3/167; G06F 3/14; G06F 3/0346; G06F 2203/011; G06F 3/011; G09G 3/20; G09G 2354/00; A06F 3/011;
(Continued)

(56) References Cited

U.S. PATENT DOCUMENTS

2003/0181291 A1* 9/2003 Ogawa ................. A63B 24/00
  482/8
2011/0270346 A1 11/2011 Frei et al.
(Continued)

FOREIGN PATENT DOCUMENTS

WO  WO 2010/067297 A1  6/2010

OTHER PUBLICATIONS

PCT International Search Report and Written Opinion, PCT Application No. PCT/US19/19241, dated Jul. 1, 2019, 17 pages.
(Continued)

*Primary Examiner* — Temesghen Ghebretinsae
*Assistant Examiner* — Ivelisse Martinez Quiles
(74) *Attorney, Agent, or Firm* — Fenwick & West LLP (57) ABSTRACT

A media system controls presentation of media content based on a detected state of a user. The user state may be detected based on biometric inputs that may be derived from IMU and/or microphone data. The biometric inputs may include a heart rate detected from IMU data representing motion of a head-mounted media processing device, a breathing rate detected from IMU data representing motion of a head-mounted media processing device, a breathing rate detected based on microphone data, or a combination thereof.

20 Claims, 5 Drawing Sheets

(51) Int. Cl.
*G06F 3/14* (2006.01)
*G06F 3/0346* (2013.01)
*A61B 5/00* (2006.01)
*G09G 3/20* (2006.01)
*G06F 13/16* (2006.01)
*G06F 3/16* (2006.01)

(52) U.S. Cl.
CPC . *A61B 2562/0219* (2013.01); *G06F 2203/011* (2013.01); *G09G 2354/00* (2013.01)

(58) Field of Classification Search
CPC ............ A61B 2562/0219; A61B 5/081; A61B 5/02444; A61B 5/721
See application file for complete search history.

(56) References Cited

U.S. PATENT DOCUMENTS

| | | | | |
|---|---|---|---|---|
| 2013/0338460 | A1* | 12/2013 | He | A61B 5/1455 600/324 |
| 2014/0316191 | A1 | 10/2014 | de Zambotti et al. | |
| 2015/0099991 | A1* | 4/2015 | Yamaguchi | A61B 5/7282 600/508 |
| 2015/0141794 | A1 | 5/2015 | Foo | |
| 2015/0265161 | A1 | 9/2015 | Hernandez et al. | |
| 2016/0029968 | A1 | 2/2016 | Lerner et al. | |
| 2017/0020398 | A1 | 1/2017 | Emadzadeh | |
| 2017/0027523 | A1* | 2/2017 | Venkatraman | A61B 5/02405 |
| 2017/0135632 | A1 | 5/2017 | Franceschetti et al. | |
| 2017/0273635 | A1* | 9/2017 | Li | A61B 5/7282 |
| 2018/0000426 | A1* | 1/2018 | Li | A61B 5/0402 |
| 2019/0046054 | A1* | 2/2019 | Li | A61B 5/0205 |
| 2019/0046077 | A1* | 2/2019 | Li | A61B 5/1102 |
| 2019/0362822 | A1* | 11/2019 | Haveri | G08B 21/0453 |

OTHER PUBLICATIONS

PCT Invitation to Pay Additional Fees and, Where Applicable, Protest Fee, PCT Application No. PCT/US19/19241, dated May 3, 2019, 4 pages.

European Patent Office, Partial Supplementary Search Report, EP Patent Application No. 19757015.3, dated Jan. 26, 2021, 14 pages.

European Patent Office, Extended European Search Report and Opinion, EP Patent Application No. 19757015.3, dated May 25, 2021, 15 pages.

* cited by examiner

ADAPTING MEDIA CONTENT TO A SENSED STATE OF A USER

CROSS-REFERENCE TO RELATED APPLICATIONS

This application claims the benefit of U.S. Provisional Patent Application No. 62/634,120 filed on Feb. 22, 2018, the contents of which are incorporated by reference herein.

BACKGROUND

Technical Field

This disclosure relates generally to a media content system, and more specifically, to a media device that provides content based on a detected state of a user.

Description of the Related Art

In media content systems, it is often desirable to adapt the content served to a particular user in order to provide the user with an interactive experience. Conventionally, interactive content adapts to the user based on deliberate inputs provided by the user. For example, a user may provide inputs through a controller, voice commands, head movements, or gestures. However, such conventional media content systems cannot always adapt to the user's mind and body state because this state may not necessarily be reflected in the user's deliberate inputs. Furthermore, requiring the user to actively provide too many inputs may degrade the user's overall experience.

SUMMARY

In a first embodiment, a media processing device adapts content based on a breathing rate detected based on captured audio. The media processing device presents first content on a display device. A microphone captures ambient audio. A frequency domain transformation is performed on a current block of the ambient audio to generate a frequency spectrum of the current block. The frequency spectrum is filtered to generate a filtered frequency spectrum limited to a predefined frequency range associated with breathing noise. One or more peak frequencies in the filtered frequency spectrum are identified. A breath is detected by identifying a pattern of peak frequencies across a range of blocks that meets predefined criteria. The breathing rate is determined based on the detected breath and a history of previously detected breaths. Second content is presented on the display device based on the detected breathing rate falling within a predefined range.

In a second embodiment, a media processing device adapts content based on a breathing rate detected based on motion data. The media processing device presents first content on a display device. Motion data is obtained from an inertial measurement device. The motion data is filtered by applying a smoothing function to the motion data to generate smoothed motion data. A breath is detected based on identifying that the smoothed motion data includes movement constrained to one or more predefined amplitude ranges associated with breathing movement over a predefined time window. A breathing rate is identified based on the detected breath. Second content is presented on the display device responsive to the detected breathing rate falling within a predefined breathing rate range.

In a third embodiment, a media processing device adapts content based on a heart rate detected based on motion data. The media processing device presents first content on a display device. Motion data is obtained from an inertial measurement device. The motion data is filtered by applying a smoothing function to the motion data to generate smoothed motion data. A heart beat is detected based on identifying that the smoothed motion data includes movement within a predefined amplitude range. A heart rate is identified based on the detected heart beat. The second content is presented on the display device responsive to the detected heart rate falling within a predefined heart rate range.

Embodiment may include a method, a non-transitory computer-readable storage medium, and a computer device for performing the above described processes.

BRIEF DESCRIPTIONS OF THE DRAWINGS

The disclosed embodiments have other advantages and features which will be more readily apparent from the following detailed description of the invention and the appended claims, when taken in conjunction with the accompanying drawings, in which:

DETAILED DESCRIPTION

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Figure 1:
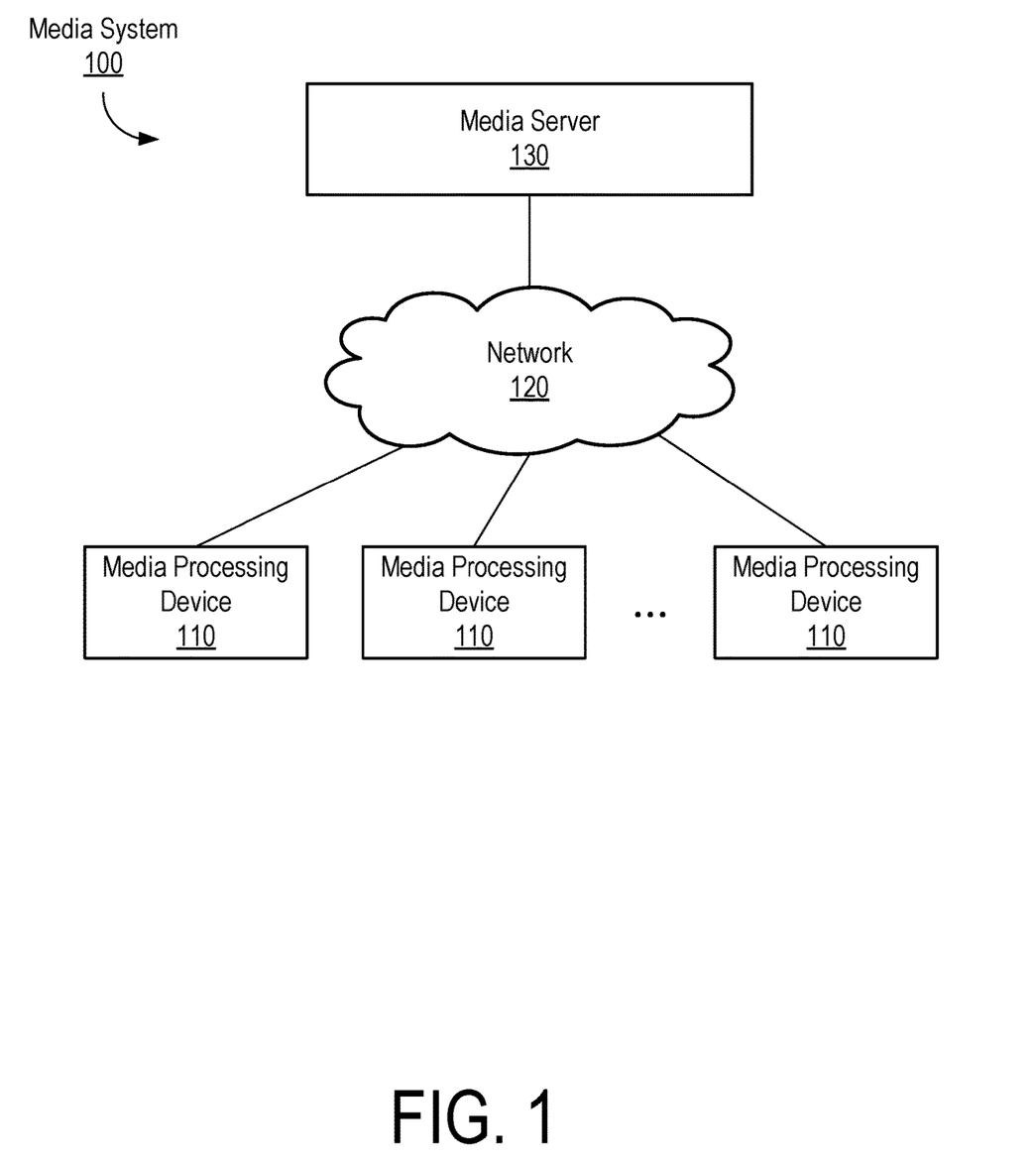
FIG. 1 illustrates an example embodiment of a media system.

FIG. 1 is a block diagram of a media system 100, according to one embodiment. The media system 100 includes a network 120, a media server 130, and a plurality of media processing devices 110. In alternative configurations, different and/or additional components may be included in the media content system 100.

The media processing device 110 comprises a computer device for processing and presenting media content such as audio, images, video, or a combination thereof. The media processing device 110 may furthermore detect various inputs including voluntary user inputs (e.g., input via a controller, voice command, body movement, or other convention control mechanism) and various biometric inputs (e.g., breathing patterns, heart rate, etc.). The media processing device 110 may control the presentation of the media content in response to the inputs. The media processing device 110 may comprise, for example, a mobile device, a tablet, a laptop computer, or a desktop computer. In an embodiment, the media processing device 110 may include a head-mounted display such as a virtual reality headset or an augmented reality headset. An embodiment of a media processing device 110 is described in further detail below with respect to FIG. 2.

The media server 130 comprises one or more computing devices for delivering media content to the media processing devices 110 via the network 120. For example, the media server 130 may stream media content to the media processing devices 110 to enable the media processing devices 110 to present the media content in real-time or near real-time. Alternatively, the media server 130 may enable the media processing devices 110 to download media content to be stored on the media processing devices 110 and played back locally at a later time.

The network 120 may include any combination of local area and/or wide area networks, using both wired and/or wireless communication systems. In one embodiment, the network 120 uses standard communications technologies and/or protocols. In some embodiments, all or some of the communication links of the network 120 may be encrypted using any suitable technique.

Various components of the media system 100 of FIG. 1 such as the media server 130 and the media processing devices 110 can each include one or more processors and a non-transitory computer-readable storage medium storing instructions therein that when executed cause the one or more processors to carry out the functions attributed to the respective devices described herein.

Figure 2:
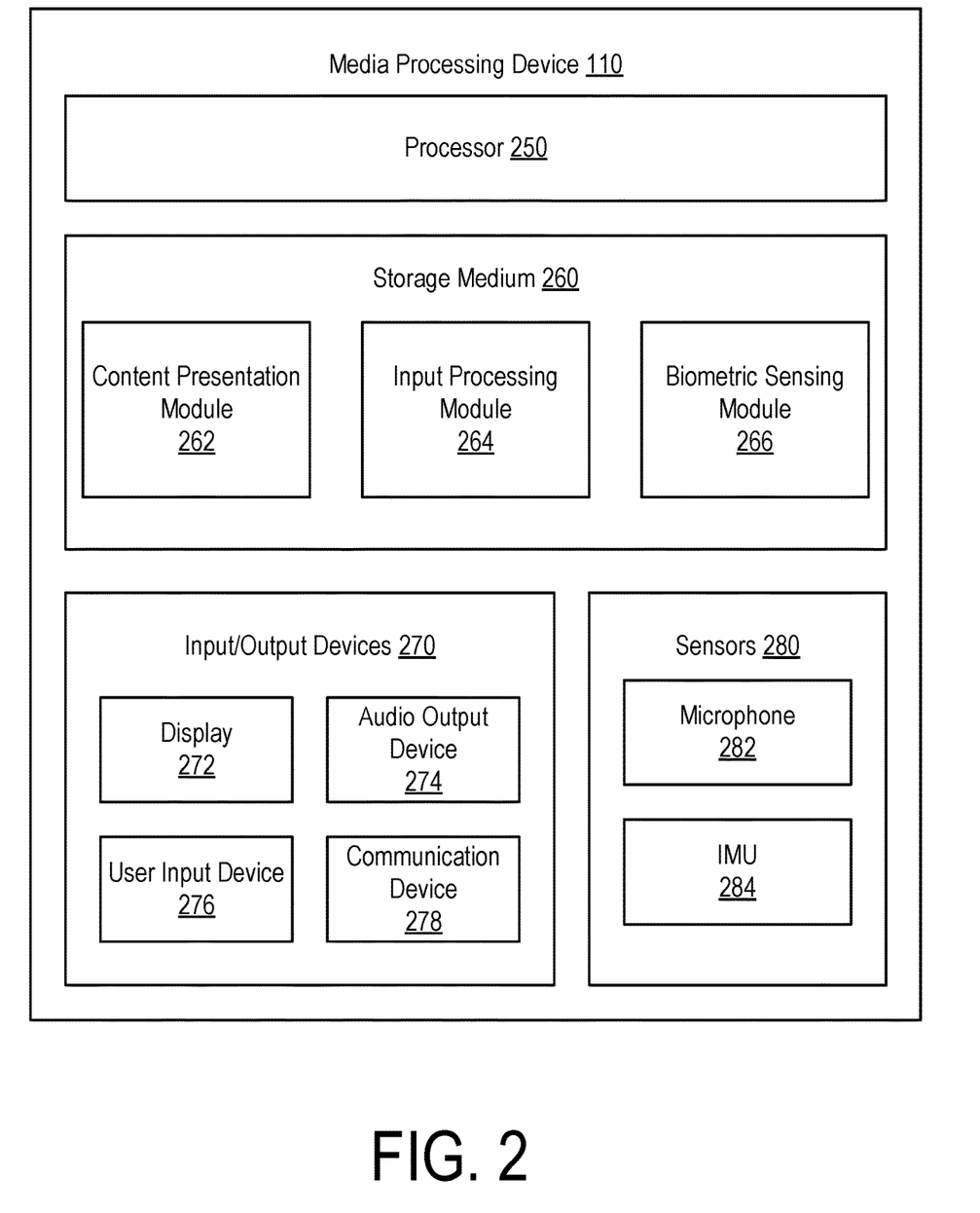
FIG. 2 illustrates an example embodiment of a media processing device.

FIG. 2 is a block diagram illustrating an embodiment of a media processing device 110. In the illustrated embodiment, the media processing device 110 comprises a processor 250, a storage medium 260, input/output devices 270, and sensors 280. Alternative embodiments may include additional or different components.

The input/output devices 270 include various input and output devices for receiving inputs to the media processing device 110 and providing outputs from the media processing device 110. In an embodiment, the input/output devices 270 may include a display 272, an audio output device 274, a user input device 276, and a communication device 278. The display 272 comprises an electronic device for presenting images or video content such as an LED display panel, an LCD display panel, or other type of display. The audio output device 274 may include one or more integrated speakers or a port for connecting one or more external speakers to play audio associated with the presented media content. The user input device can comprise any device for receiving user inputs such as a touchscreen interface, a game controller, a keyboard, a mouse, a joystick, a voice command controller, a gesture recognition controller, or other input device. The communication device 278 comprises an interface for receiving and transmitting wired or wireless communications with external devices (e.g., via the network 120 or via a direct connection). For example, the communication device 278 may comprise one or more wired ports such as a USB port, an HDMI port, an Ethernet port, etc. or one or more wireless ports for communicating according to a wireless protocol such as Bluetooth, Wireless USB, Near Field Communication (NFC), etc.

The sensors 280 capture various sensor data that can be provided as additional inputs to the media processing device 110. For example, the sensors 240 may include a microphone 282 and an inertial measurement unit (IMU) 284. The microphone 282 captures ambient audio by converting sound into an electrical signal that can be stored or processed by the media processing device 110. The IMU 284 comprises an electronic device for sensing movement and orientation. For example, the IMU 284 may comprise a gyroscope for sensing orientation or angular velocity and an accelerometer for sensing acceleration. The IMU 284 may furthermore process data obtained by direct sensing to convert the measurements into other useful data, such as computing a velocity or position from acceleration data. In an embodiment, the IMU 284 may be integrated with the media processing device 110. Alternatively, the IMU 284 may be communicatively coupled to the media processing device 110 but physically separate from it so that the IMU 284 could be mounted in a desired position on the user's body (e.g., on the head or wrist).

The storage medium 260 (e.g., a non-transitory computer-readable storage medium) stores instructions executable by the processor 250 for carrying out functions attributed to the media processing device 110 described herein. In an embodiment, the storage medium 260 includes a content presentation module 262, an input processing module 264, and a biometric sensing module 266. The content presentation module 262 presents media content via the display 272 and the audio output device 274. The content presentation module 262 may adapt its content based on information received from the input processing module 264 and the biometric sensing module 266. The input processing module 262 processes inputs received via the user input device 276 and provides processed input data that may control the output of the content presentation module 262. The biometric sensing module 266 obtains sensor data from the sensors 280 such as audio data and IMU data (e.g., accelerometer data, gyro data, or other inertial measurements). The biometric sensing module 266 processes the sensor data to derive biometric information such as a breathing rate and heart rate. For example, breathing rate may be detected from audio data, from IMU data, or from a combination thereof as will be described in further detail below. Furthermore, heart rate may be detected based on IMU data as will be described in further detail below. These types of biometric data can be utilized to determine a mind and body state of the user that may not be apparent from voluntary inputs alone. For example, a measure of relaxation may be determined in an automated way based on the detected heart rate and breathing pattern. This state information may be utilized to automatically adapt the presentation of content based on the user's detected mind and body state.

In an example application, an interactive media application may guide a user through a meditation experience. In this example experience, a user may be taken through a first exercise to guide the user towards a target breathing rate and heart rate indicative of a particular state of relaxation. The user's breathing and heart rate can be detected throughout the experience and the content may be updated to move on to a subsequent exercise once the target breathing rate and heart rate are achieved. Alternatively, if the user is having difficulty achieving the target breathing rate and heart rate, the content may be updated to provide the user with an alternative exercise (e.g., a simpler exercise). Furthermore, the breathing rate and heart rate (or an overall relaxation state metric) may be provided to the user as real-time feedback via a graphical user interface, or the information may be logged to provide to the user as feedback after completing the experience.

In other examples, heart rate and breathing rate can be used in other types of lifestyle applications that provide feedback to the user relating to a detected rest state, level of focus, or other information. In gaming applications, for example, avatars in a virtual room may display emotions consistent with the user's detected mind and body state derived from the detected breathing rate and heart rate. Similarly, other characters in the game may interact with the user's character based on the detected state. In medical applications, the detected breathing rate and heart rate may be used as a diagnostic tool to identify medical conditions such as shortness of breath or symptoms of a heart condition. In dating or social applications, real-time emoticons may be generated that reflect the user's state. Furthermore, the user may be given a test that measures emotional response (derived from the heart rate and breathing rate) to particular inputs that may be useful to identify potential dating matches. In other applications, the user's state may be utilized to provide feedback to music or movie creators to gauge how users react when listening to music or watching a movie.

Figure 3:
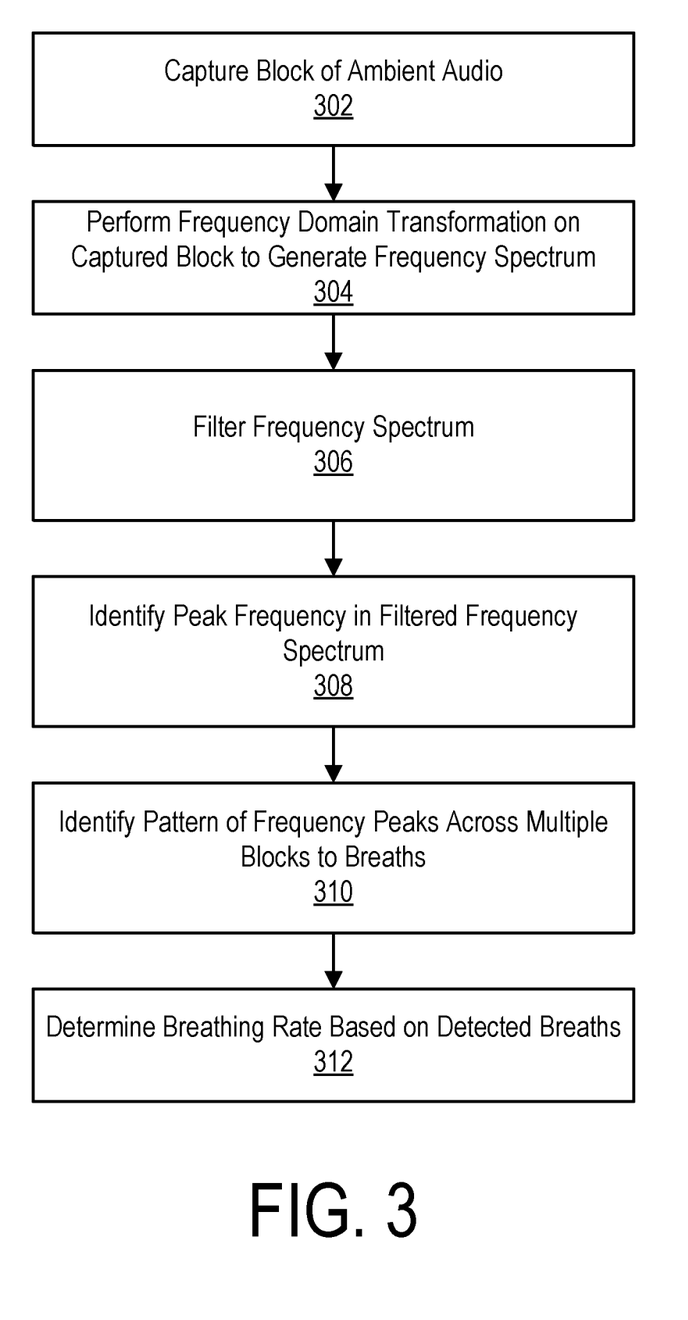
FIG. 3 illustrates an example embodiment of a process for detecting a breathing rate based on audio.

FIG. 3 illustrates an embodiment of a process for detecting a breathing rate based on audio data. The media processing device 110 captures 302 a block of ambient audio data (e.g., using the microphone 282). Here, an audio block represents a sequence of audio samples within a limited time range. For example, audio may be captured at a rate of approximately 48,000 samples per second and may be grouped into blocks at a rate of approximately 60-90 blocks per second. A frequency domain transformation is performed 304 on the block to generate a frequency spectrum for the block. For example, in one embodiment, a Fast Fourier Transform (FFT) is performed on the block to generate the frequency spectrum. The frequency spectrum for a given block may comprise a plurality of discrete frequency bins (e.g., 1024 bins) covering the range of, for example, 0-24 kHz such that each frequency bin corresponds to a different sub-range and each frequency bin represents an amplitude of the frequency components within the sub-range. The media processing device 110 may filter 306 the frequency spectrum. Here, the filtering may include applying a band-limiting filter to limit the frequency spectrum to the typical frequency ranges found in an audio capture of breathing. For example, in one embodiment, the media processing device 110 may filter the frequency spectrum to limit it to a range of approximately 4 kHz-5 kHz (e.g., by discarding bins outside of this frequency range). Additionally, the filtering may include applying a noise filter to the block. For example, in one embodiment, an adaptive noise spectrum is generated that is updated at each block as a weighted combination of a cumulative noise spectrum and the frequency spectrum for the current block. For example, the noise spectrum Noise for a block i may be represented as:

$$Noise_i = \alpha \cdot FFT'_i + (1-\alpha) \cdot Noise_{i-1}$$

where $FFT'_i$ is the pre-noise filtered frequency spectrum for the block i, and $\alpha$ is a filtering parameter such that $0<\alpha<1$ (e.g., $\alpha=0.05$). The noise spectrum may be subtracted from the frequency spectrum to remove the noise:

$$FFT_i = FFT'_i - Noise_i$$

where $FFT_i$ is the noise filtered frequency spectrum.

The media processing device 110 identifies 308 one or more peak frequencies in the noise filtered frequency spectrum of the block. For example, in one embodiment, a single peak frequency is identified for each block that corresponds to the frequency having the largest amplitude within the block. Alternatively, a set of peak frequencies may be identified for each block corresponding to the N frequencies having the largest amplitudes for each block (e.g., N=3). In another embodiment, the peak frequencies may correspond to any frequencies having amplitudes exceeding a predefined threshold amplitude. In this case, the number of peak frequencies in each frame may be variable, and some frames may not include any peak frequencies. In embodiments where multiple frequency peaks are identified in a block, the media processing device 110 may average the amplitudes of the frequency peaks within the block to generate an overall frequency peak amplitude. Furthermore, additional smoothing filter may be applied by averaging the current overall frequency peak amplitude with overall frequency peak amplitudes for prior blocks. This processing results in a sequence of smoothed frequency peak amplitudes over a sequence of blocks. The media processing device 110 identifies 310 a peak frequency pattern across multiple blocks that substantially matches an expected pattern corresponding to inhales and exhales. For example, in one embodiment, the media processing device 110 scans audio using a sliding time window of predefined length (e.g., a window of 0.2 seconds) to identify windows in which at least a threshold percentage (e.g., 80%) of the smoothed frequency peak amplitudes are within one or more predefined amplitude ranges (e.g., amplitude ranges consistent with human inhales or exhales). Time windows meeting the above criteria and occurring within a predefined time range of each other (e.g., a time range consistent with normal human breathing rate) are then identified. In an embodiment, a pattern of time windows are identified in which the amplitude ranges of the smoothed frequency peaks alternately correspond to the ranges associated with inhales and exhales. For example, the media processing device 110 identifies first time windows in which the amplitudes of the smoothed frequency peaks correspond to a first amplitude range associated with an inhale, identifies second time windows in which the amplitudes of the smoothed frequency peaks correspond to a second amplitude range associated with an exhale, and detects an alternating pattern of inhales and exhales. In this case, a pair of time windows meeting the above criteria for an inhale and exhale are detected as a breath. The breathing rate may then be determined 312 based on a rate of the detected breaths that meet the above criteria. For example, the breathing rate may be based on an average time or a median time between breaths meeting the above criteria and that is within a predefined reasonable range of expected breathing rates.

Figure 4:
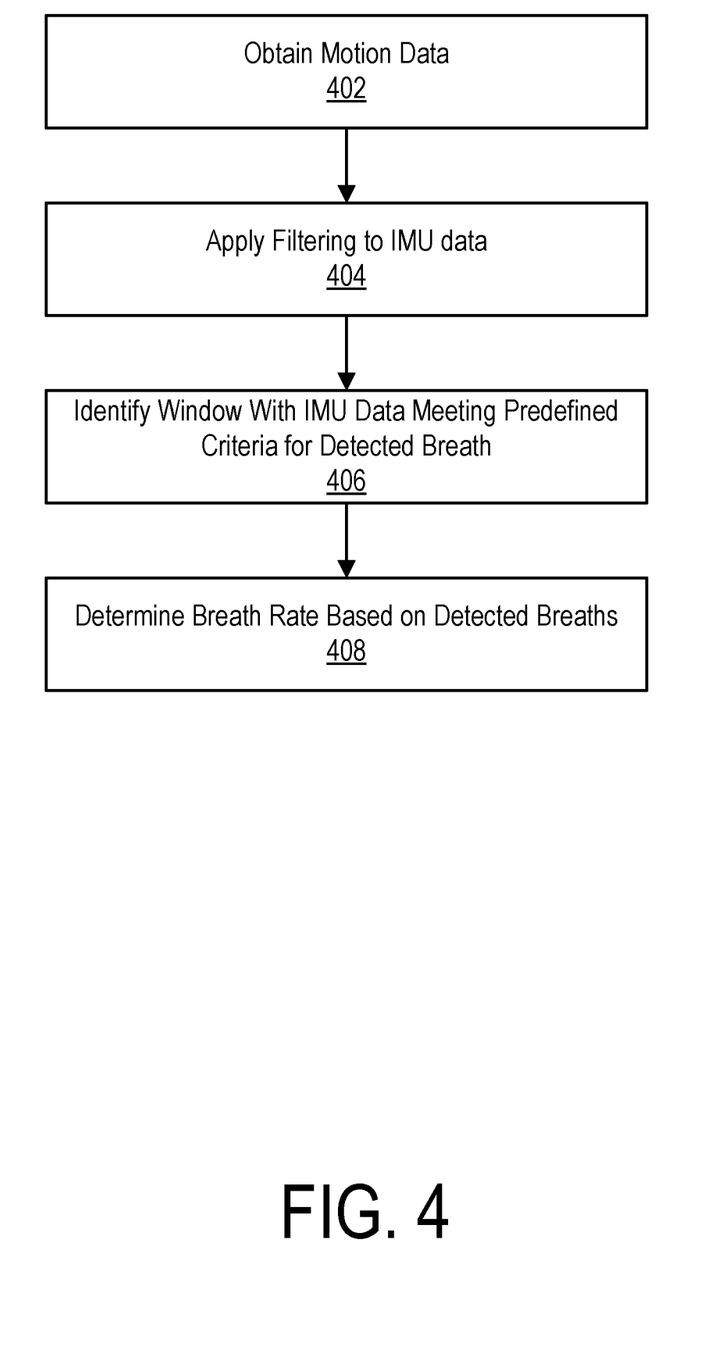
FIG. 4 illustrates an example embodiment of a process for detecting a breathing rate based on motion data.

FIG. 4 illustrates an embodiment of a process for determining a breathing rate from IMU data. The media processing device 110 obtains 402 IMU data (e.g., from the IMU 284 in a head-mounted sensor) that represents the change in angle and change in position relative to a prior time block (e.g., at a rate of 60-90 blocks per second). Here, the position may comprise a three-dimensional position vector representing a change in (x, y, z) coordinates of the position. The angle may comprise a three-dimensional angle vector representing a change in orientation in three-dimensional space. The media processing device 110 applies 404 filters to the obtained IMU data. For example, a smoothing filter may be applied by combining the current angle and position values with prior values. For example:

$$\Delta x_i = \beta \Delta x'_i + (1-\beta)\Delta x_{i-1}$$

$$\Delta \theta_i = \gamma \Delta \theta'_i + (1-\gamma)\Delta \theta_{i-1}$$

where $\Delta x'_i$ is the pre-filtered change in position for the block i, $\Delta x_i$ is the smoothed change in position for the block i, $\beta$ is a first filtering parameter (e.g., $\beta=0.7$), $\Delta \theta'_i$ is the pre-filtered change in angle for the block i, $\Delta \theta_i$ is the smoothed change in angle for the block i, and $\gamma$ is a second filtering parameter (e.g., $\gamma=0.7$). The media processing device 110 then identifies 406 a window of smoothed IMU data meeting predefined criteria for a detected breath. For example, the media processing device identifies a window in which the smoothed change in position values and/or the smoothed change in angle values is within a predefined expected range over the time window to identify breaths. For example, movements outside of respective predefined ranges for the smoothed change in position and smoothed change in angle values may be filtered out (e.g., discarded). Here, the predefined range associated with the smoothed change in position may correspond to the expected vertical movement amplitude indicative of a breath (e.g., 0.8-10 millimeters in the vertical direction). Similarly, the predefined range associated with the smoothed change in angle may correspond to an expected change in pitch or rotation about the x-axis (i.e., a left-right axis parallel with a width of the human body) indicative of a breath. Breaths may be detected based on the filtered and smoothed IMU data. For example, for each window of a sliding time window (e.g., 0.2 second windows), the filtered and smoothed IMU data is analyzed to detect a window in which IMU data is in within the respective ranges for both position and angle. In an embodiment, the lower bound of the range may decrease from the beginning of the time window to the end of the time window to correspond to an expecting slowing of the head movement towards the end of an inhale. For example, the predefined amplitude range for vertical position may be set to 0.8-10 millimeters at the beginning of the time window and decrease to 0.4-10 millimeters at the end of the time window. In an embodiment, a breath is dedicated when both the position and angle data meet the above criteria for a given time window. In alternative embodiments, a breath may be dedicated when either one of the position or angle data meet the above criteria for a given time window. In some embodiments, the IMU 284 may obtain only one of the position or angle data without necessarily obtaining both.

In an embodiment, instead of only detecting inhales, the media processing device 110 may separately detect inhales and exhales and only detect a breath when both are detected in relative time proximity. To detect an exhale, the respective ranges for comparing the IMU data may be different than the ranges for detecting an inhale. For example, when detecting an inhale, the predefined range for the smoothed change in position may comprise a positive value in the vertical direction to represent upward movement of the head. When detecting an exhale, the predefined range for the smoothed change in position may comprise a negative value in the vertical direction to represent downward movement of the head. Furthermore, when detecting an inhale, the predefined range for the smoothed change in angle may comprise a positive value about the x-axis to represent front-to-back rotation of the head. When detecting an exhale, the predefined range for the smoothed change in angle may comprise a negative about the x-axis to represent back-to-front rotation of the head. Furthermore, when detecting an exhale, the lower bound of the predefined range may increase from the beginning of the time window to the end of the time window. The breathing rate may then be determined 408 based on the detected breaths over a range of time windows (e.g., based on an average or median time period between detected breaths).

In another alternative embodiment, a combination of IMU data and audio data may be used to identify the breathing patterns. For example, the media processing device 110 may concurrently run the processes of FIG. 3 and FIG. 4 to determine when either one of the processes detect a breath. If a breath is detected with the IMU data but not the audio data, the amplitude audio range may be extended by a predefined percentage (e.g., 15%). If a breath is then detected based on the audio data, the breath detection is confirmed. Otherwise, no breath is detected.

Figure 5:
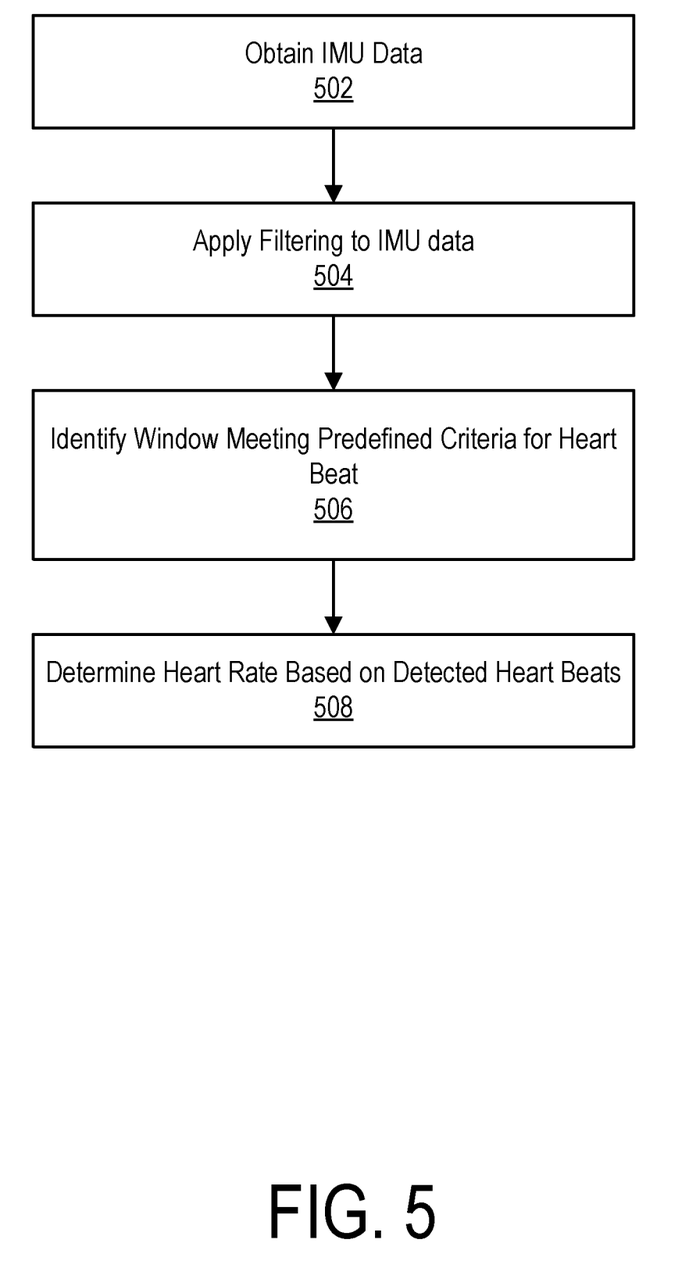
FIG. 5 illustrates an example embodiment of a process for detecting a heart rate based on motion data.

FIG. 5 illustrates an example embodiment of a process for detecting a heart rate using IMU data. The media processing device 110 obtains 502 IMU data similar to detecting the breathing rate described above. The media processing device 110 applies 504 filtering to the IMU data. Here, the filtering may include the same smoothing filter used when identifying breathing as described above, to obtain smoothed change in position $\Delta x_i$ and smoothed change in angle $\Delta \theta_i$ for each time block i. In this process, the obtained values may be additionally filtered to discard movements determined to be related to breathing. The media processing device 110 identifies 506 a window of smoothed IMU data meeting predefined criteria for a detected heart beat. For example, the media processing device 110 identifies a window in which the smoothed change in position and/or the smoothed change in angle values are within a predefined expected range that is indicative of a heart beat. Here, the media processing device 110 may filter the smoothed position data to filter out changes in position outside the range of 0.1-1 millimeter in the vertical direction. The media processing device 110 may then detect heart beats from the filtered data. For example, the media processing device 110 may detect a heart beat when both the smoothed change in position and the smoothed change in angle are within their respective predefined ranges. In alternative embodiments, a heart beat may be dedicated when either one of the position or angle data meet the above criteria. In some embodiments, the IMU 284 may obtain only one of the position or angle data without necessarily obtaining both.

The heart rate is determined 508 based on the timing of the detected heart beats. In an embodiment, the media processing device 110 may enforce a smoothing function on the detected heart rate to reduce erroneous detections. Here, the media processing device 110 may identify a sequence of time differences between consecutive detected heart beats. The values may be compared against a baseline heart rate (e.g., a previously determined heart rate for a preceding time period) to determine if the time differences are within a predefined threshold percentage (e.g., 10%) of the baseline heart rate. For example, if the time differences are determined to be {0.85 seconds, 0.84 seconds, 0.87 seconds, . . . } and the previously detected heart rate corresponds to 0.4 second time periods, the media processing device 110 determines that the data likely does not correspond to heart rate because heart rate generally does not change that quickly. However, if a heart rate within the threshold range of the previously determined value is not detected within an allowed time window and the data is self-consistent with a different heart rate, it may be determined that the previously detected heart rate was erroneous and the heart rate may be reset based on the current data. Generally, the media processing device 110 may identify a heart rate corresponding to beats occurring at a rate of approximately 45-120 cycles per minute, which is the typical range of heart rates.

In an embodiment, the breathing rate and heart rate may be combined (optionally with other inputs or biometric data) to generate an overall metric representing a state of the user. For example, the metric may represent a measure of the user's relaxation state. The overall metric may be generated, for example, as a weighted combination of the heart rate and breathing rate.

In other alternative embodiments, all or parts of the processes of FIGS. 3-5 may be performed on the media server 130 instead of on the media processing devices 110. For example, in one embodiment, the media processing device 110 may transmit the sensed audio data and IMU data to the media server 130, and the media server 130 may calculate the breathing rate and heart rate based on the received data.

Throughout this specification, some embodiments have used the expression "coupled" along with its derivatives. The term "coupled" as used herein is not necessarily limited to two or more elements being in direct physical or electrical contact. Rather, the term "coupled" may also encompass two or more elements that are not in direct contact with each other, but yet still co-operate or interact with each other.

Likewise, as used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Upon reading this disclosure, those of skill in the art will appreciate still additional alternative structural and functional designs for the described embodiments as disclosed from the principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the scope defined in the appended claims.

The invention claimed is:

1. A method for adapting content based on detecting a heart rate, the method comprising:
   presenting first content on a display device;
   obtaining motion data from an inertial measurement device;
   filtering the motion data to apply a smoothing function to the motion data to generate smoothed motion data;
   detecting a heart beat based on identifying that the smoothed motion data comprises a change in pitch of the inertial measurement device about an axis parallel to a width of a human body within a first predefined amplitude range;
   identifying the heart rate based on the detected heart beat; and
   presenting second content on the display device responsive to the detected heart rate falling within a predefined heart rate range.

2. The method of claim 1, wherein detecting the heart beat is further based on identifying that the smoothed motion data includes a change in vertical position of the inertial measurement device within a second predefined amplitude range.

3. The method of claim 1, wherein identifying the heart rate comprises:
   obtaining a baseline heart rate for a time period;
   determining time differences between detected consecutive heart beats;
   comparing the time differences between the detected consecutive heart beats to the baseline heart rate; and
   responsive to determining, based on the comparison, that the time differences between the detected consecutive heart beats are within a predefined percentage of the baseline heart rate, determining the heart rate from an average rate corresponding to the time differences between the detected consecutive heart beats.

4. The method of claim 3, further comprising:
   responsive to not detecting any heart rates corresponding to time differences within the predefined percentage of the baseline heart rate over a predefined allowed time window, resetting the baseline heart rate to correspond to the heart rate determined from the average rate corresponding to the time differences between the detected consecutive heart beats.

5. The method of claim 1, wherein identifying the heart rate comprises:
   obtaining a baseline heart rate for a time period;
   determining time differences between detected consecutive heart beats;
   comparing the time differences between the detected consecutive heart beats to the baseline heart rate;
   responsive to determining, based on the comparison, that the time differences are not within a predefined percentage of the baseline heart rate, determining the heart rate corresponds to the baseline heart rate.

6. The method of claim 1, wherein the display device comprises a head-mounted display device.

7. A method for adapting content based on detecting heart rates, the method comprising:
   presenting first content on a display device;
   obtaining motion data from an inertial measurement device;
   filtering the motion data to apply a smoothing function to the motion data to generate smoothed motion data;
   detecting consecutive heart beats based on identifying that the smoothed motion data includes movement within a predefined amplitude range;
   obtaining a baseline heart rate for a time period;
   determining time differences between the detected consecutive heart beats;
   comparing the time differences between the detected consecutive heart beats to the baseline heart rate;
   responsive to determining, based on the comparison, that the time differences between the detected consecutive heart beats are within a predefined percentage of the baseline heart rate, determining a heart rate from an average rate corresponding to the time differences between the detected consecutive heart beats; and presenting second content on the display responsive to the heart rate falling within a predefined heart rate range.

8. The method of claim 7, further comprising:
responsive to not detecting any heart rates corresponding to time differences within the predefined percentage of the baseline heart rate over a predefined allowed time window, resetting the baseline heart rate to the heart rate determined from the average rate corresponding to the time differences between the detected consecutive heart beats.

9. The method of claim 7, wherein the average rate is an average of the time differences between the detected consecutive heart beats.

10. The method of claim 7, further comprising:
responsive to determining, based on the comparison, that the time differences are not within the predefined percentage of the baseline heart rate, determining the heart rate corresponds to the baseline heart rate.

11. The method of claim 7, wherein the display device comprises a head-mounted display device.

12. A non-transitory computer-readable storage medium storing instructions for adapting content based on detecting a heart rate, the instructions when executed by a processor causing the processor to perform steps including:
presenting first content on a display device;
obtaining motion data from an inertial measurement device;
filtering the motion data to apply a smoothing function to the motion data to generate smoothed motion data;
detecting a heart beat based on identifying that the smoothed motion data comprises a change in pitch of the inertial measurement device about an axis parallel to a width of a human body within a first predefined amplitude range;
identifying the heart rate based on the detected heart beat; and
presenting second content on the display device responsive to the detected heart rate falling within a predefined heart rate range.

13. The non-transitory computer-readable storage medium of claim 12, wherein detecting the heart beat is further based on identifying that the smoothed motion data includes a change in vertical position of the inertial measurement device within a second predefined amplitude range.

14. The non-transitory computer-readable storage medium of claim 12, wherein identifying the heart rate comprises:
obtaining a baseline heart rate for a time period;
determining time differences between detected consecutive heart beats;
comparing the time differences between the detected consecutive heart beats to the baseline heart rate; and
responsive to determining, based on the comparison, that the time differences between the detected consecutive heart beats are within a predefined percentage of the baseline heart rate, determining the heart rate from an average rate corresponding to the time differences between the detected consecutive heart beats.

15. The non-transitory computer-readable storage medium of claim 14, wherein identifying the heart rate comprises:

responsive to not detecting any heart rates corresponding to time differences within the predefined percentage of the baseline heart rate over a predefined allowed time window, resetting the baseline heart rate to the heart rate determined from the average rate corresponding to the time differences between the detected consecutive heart beats.

16. The non-transitory computer-readable storage medium of claim 12, wherein identifying the heart rate comprises:
obtaining a baseline heart rate for a time period;
determining time differences between detected consecutive heart beats;
comparing the time differences between the detected consecutive heart beats to the baseline heart rate;
responsive to determining, based on the comparison, that the time differences are not within a predefined percentage of the baseline heart rate, determining the heart rate corresponds to the baseline heart rate.

17. A non-transitory computer-readable storage medium storing instructions for adapting content based on detecting heart rates, the instructions when executed by a processor causing the processor to perform steps including:
presenting first content on a display device;
obtaining motion data from an inertial measurement device;
filtering the motion data to apply a smoothing function to the motion data to generate smoothed motion data;
detecting consecutive heart beats based on identifying that the smoothed motion data includes movement within a predefined amplitude range;
obtaining a baseline heart rate for a time period;
determining time differences between the detected consecutive heart beats;
comparing the time differences between the detected consecutive heart beats to the baseline heart rate;
responsive to determining, based on the comparison, that the time differences between the detected consecutive heart beats are within a predefined percentage of the baseline heart rate, determining a heart rate from an average rate corresponding to the time differences between the detected consecutive heart beats; and
presenting second content on the display responsive to the heart rate falling within a predefined heart rate range.

18. The non-transitory computer-readable storage medium of claim 17, the instructions when executed further causing the processor to perform steps including:
responsive to not detecting any heart rates corresponding to time differences within the predefined percentage of the baseline heart rate over a predefined allowed time window, resetting the baseline heart rate to the heart rate determined from the average rate corresponding to the time differences between the detected consecutive heart beats.

19. The non-transitory computer-readable storage medium of claim 17, wherein the average rate is an average of the time differences between the detected consecutive heart beats.

20. The non-transitory computer-readable storage medium of claim 17, further comprising:
responsive to determining, based on the comparison, that the time differences are not within the predefined percentage of the baseline heart rate, determining the heart rate corresponds to the baseline heart rate.

* * * * *